United States Patent
Washburn et al.

[11] Patent Number: 5,466,715
[45] Date of Patent: Nov. 14, 1995

[54] 3,4-DISUBSTITUTED PHENOLS-IMMUNOMODULATING AGENTS

[75] Inventors: William N. Washburn, Titusville, N.J.; Barbara B. Lussier, Rochester, N.Y.; Carl R. Illig, Phoenixville; Lee H. Latimer, Wayne, both of Pa.

[73] Assignee: Sterling Winthrop Inc., New York, N.Y.

[21] Appl. No.: 208,396

[22] Filed: Mar. 8, 1994

Related U.S. Application Data

[60] Continuation-in-part of Ser. No. 81,900, Jun. 25, 1993, abandoned, which is a division of Ser. No. 816,503, Dec. 31, 1991, Pat. No. 5,258,407.

[51] Int. Cl.$^6$ .................. A61K 31/165; A61K 31/16
[52] U.S. Cl. .................. 514/618; 514/619; 514/622; 514/629
[58] Field of Search .................. 514/256, 599, 514/613, 617, 618, 619, 622, 629

[56] References Cited

U.S. PATENT DOCUMENTS 5,032,617  7/1991  Lee et al. .................. 514/617

OTHER PUBLICATIONS

Gillis et al., Nature, 268, 154–156, 1977.
Farrar J. et al., J. Immunol, 121, 1353–1360, 1978.
Gillis et al., J. Immunol 120, 2027–2033, 1978.
Gillis et al, J. Immunol 124, 1954–1962 1980.
Gillis et al, J. Immunol 125, 2570–2578, 1980.
Gillis et al, J. Exp Med, 152, 1709–1719, 1980.

*Primary Examiner*—Jerome D. Goldberg
*Attorney, Agent, or Firm*—William J. Davis; Imre (Jim) Balogh

[57] ABSTRACT

Certain 3,4-disubstituted phenols and pharmaceutically acceptable salts thereof are provided which mimic IL-1 activity by inducing IL-2 synthesis and subsequent IL-2 receptor expression. Specifically, the invention provides compounds of Formula I and acid addition salts thereof:

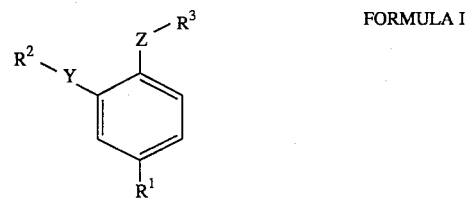

FORMULA I wherein

Y is

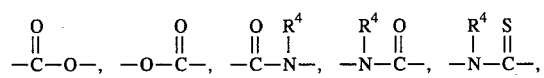

$NHSO_2$ or $SO_2NH$ where $R^4$ is H;

Z is —O—, —NH—, —NR—, —S—, or other heteroatoms capable of hydrogen bonding with $R^4$ to give a preferred conformation;

R is alkyl;

$R^1$ is —OH;

$R^2$ is H, alkyl, cycloalkyl, aralkyl, substituted or unsubstituted aryl, or a substituted or unsubstituted nitrogen heterocyclic group having 4 to 5 nuclear carbon atoms; and $R^3$ is a lipophilic moiety selected from the group consisting of substituted $C_1$–$C_{10}$ alkyl, $C_3$–$C_{16}$ cycloalkyl and 2,4-di-t-pentylphenyl.

12 Claims, No Drawings

3,4-DISUBSTITUTED PHENOLS-IMMUNOMODULATING AGENTS

This application is a continuation-in-part of application Ser. No. 08/081,900 filed on Jun. 25, 1993 which is, in turn, a division of application Ser. No. 07/816,503 filed on Dec. 31, 1991, now U.S. Pat. No. 5,258,407.

BACKGROUND OF THE INVENTION

1. Field of the Invention

The present invention relates to 3,4-disubstituted phenols, methods for their preparation and, to their use as immunomodulating agents. More specifically, the present invention relates to 3,4-disubstituted phenols having interleukin 1 (hereinafter IL-1) mimetic activity, which can be used as a stimulant of the immune functions.

2. Reported Developments

IL-1 is a 17kD polypeptide hormone which induces a wide range of biological effects by binding IL-1 to a specific receptor protein on responsive cells. Some of the activities of IL-1 include: induction of IL-2 secretion from T cells, induction of fibroblasts to secrete PGE, stimulation of osteoclasts to resorb bone, triggering the appearance of CSF receptors on stem cell progenitors, increasing synthesis of CSF's, activation of T and B cells, induction of cartilage destruction in joints, elevation of collagenase levels in synovial fluid and action as an endogenous pyrogen.

Because of the multiple activities of IL-1, a variety of uses for compounds influencing these responses have been envisioned. An IL-1 agonist or mimetic would have therapeutic applications as an immunostimulant, an anticancer agent or in inducing haemopoesis.

IL-1 has been produced in the prior art by inducing secretion thereof by normal macrophages/monocytes of peripheral blood by means of application of an inducing agent of bacterial origin. IL-1 has also been produced by culturing a human leukemic cell line of haematopoietic origin by means of application of phorbols as inducing agents. Another approach to provide for IL-1 activity is disclosed in U.S. Pat. No. 4,762,914 which teaches the production of truncated protein of IL-1 made by a genetic engineering procedure. The so obtained biologically active human IL-1 protein is said to be useful to induce the production of IL-2 by activated T-cells. Still another approach to provide IL-1 activity is disclosed in U.S. Pat. No. 4,774,320 which concerns the preparation and use of the following peptide that mimics human IL-1 activity:

Val-Gln-Gly-Glu-Glu-Ser-Asn-Asp-Lys-X
where

X cysteine (Cys), OH, $NH_2$, benzyl ester or an alkyl ester group having a number of carbon atoms from 1 to 7.

IL-2, also known as T cell growth factor, has been found to influence cell-mediated immune responses in mammals, such as: enhancement of thymocyte mitogenesis; production of cytotoxic T lymphocytes; promotion of proliferation of antigert specific killer T cell lines; and promotion of antierythrocyte placque forming cell responses.

Disruptions of the immunodefense system can be ascribed to the insufficient presence of IL-2 in the mammalian body, as a result of the lack of cells that produce IL-2, inadequate IL-2 production, or insufficient formation of IL-2 receptors (U.S. Pat. No. 4,752,573). In light of these findings by the prior art, IL-2 appears to be useful in promoting humoral and cellular immune responses and in restoring an immune deficient state to a normal immune state. Accordingly, IL-2 is indicated for medical immunotherapy against immunological disorders, including neoplastic diseases, bacterial or viral infections, immune deficient disorders and autoimmune diseases.

IL-2 has been produced in the prior art by stimulating mouse, rat or human lymphocytes with a mitogen (Gillis, S. et al., Nature, 268, 154–156, (1977), Farrat, J. et al., J. Immunol., 121, 1353–1360, (1978), Gillis, S. et al., J. Immunol., 120, 2027–2033, (1978)) or by stimulating human peripheral blood mononuclear lymphocytes with a mitogen (Gillis, S. et al., J. Immuno., 124, 1954–1962, (1980)). Gillis et al. reported the preparation of murine ILo2 from murine T cell lymphoma cell line (Gillis, S. et al. J. Immunol., 125, 2570–2578 (1980)) and preparation of human IL-2 from a human leukemia cell line (Gillis, S. et al., J. Exp. Med., 152, 1709–1719, (1980)).

Other methods of preparations, compositions and use thereof are illustrated by the following references.

U.S. Pat. No. 4,404,280 discloses a process for producing murine IL-2 from malignant neoplastic cells in vitro in a protein-containing medium. The process includes the utilization of IL-1 as a co-stimulant to induce IL-2 production.

U.S. Pat. No. 4,406,830 relates inter alia. to a process for producing a serum-free and mitogen-free IL-2 in vitro by adding glycoprotein to a serum-free and mitogen-free IL-1 preparation.

U.S. Pat. No. 4,738,927 discloses a method of producing IL-2 by isolating a gene which possesses IL-2 activity, connecting said gene with a vector DNA which is capable of replicating in a procaryotic or eucaryotic cell at a position down-stream of a promoter gene in the vector to obtain a recombinant DNA, with which the cell is transformed to produce IL-2.

U.S. Pat. No. 4,752,573 relates to the use of pterins to increase the activity of lymphokines and other cell growth factors, including IL-2.

U.S. Pat. No. 4,780,313 discloses a method for immunostimulating a warm-blooded animal by administering to said animal a substance having IL-2 activity, such as a recombinant non-glycosylated human IL-2, in combination with muramyldipeptide.

U.S. Pat. No. 4,789,658 relates to an immunoprophylactic and immunotherapeutic composition comprising grade E human IL-2 of human T-lymphocyte origin.

The utility of IL-2 to supplement immune responses and thus the need for IL-2 mediators to proliferate other effector cells, such as T-helper and suppressor cells, cytotoxic T-cells and natural killer cells (hereinafter NKC's) to promote cell-mediated immunity, is apparent from the above-described references.

It should also be noted that IL-1, or a biologically active compound that mimics IL-1 activity, plays a very important role as an immunostimulating agent by inducing IL-2 synthesis and subsequent IL-2 receptor expression.

We have now discovered a class of organic compounds which promote cell-mediated immunity based on their capability to elevate IL-2 and granulocyte macrophage colony stimulating factor (hereinafter GM-CSF) levels in vitro and thus proliferate effector cells, such as cytotoxic T-cells lines and other subpopulations of T-cells.

SUMMARY OF THE INVENTION

In accordance with the present invention, certain 3,4-disubstituted phenols and pharmaceutically acceptable salts thereof are provided which mimic IL-1 activity by inducing IL-2 synthesis and subsequent IL-2 receptor expression.

Specifically, the invention provides compounds of Formula I and acid addition salts thereof:

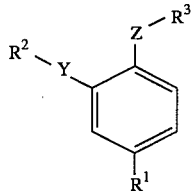

FORMULA I wherein
Y is

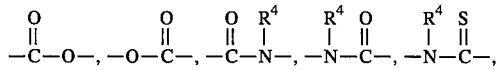

$NHSO_2$ or $SO_2NH$ where $R^4$ is H;

Z is —O—, —NH—, —NR—, —S—, or other heteroatoms capable of hydrogen bonding with $R^4$ to give a preferred conformation;

R is alkyl;

$R^1$ is —OH;

$R^2$ is H, alkyl, cycloalkyl, aralkyl, substituted or unsubstituted aryl, or a substituted or unsubstituted nitrogen heterocyclic group having 4 to 5 nuclear carbon atoms; and $R^3$ is a lipophilic moiety selected from the group consisting of substituted $C_1$–$C_{10}$ alkyl, $C_3$–$C_{16}$ cycloalkyl and 2,4-di-t-pentylphenyl.

DETAILED DESCRIPTION OF THE INVENTION

As employed above and throughout the specification the following terms, unless otherwise indicated, shall be understood to have the following meaning:

The "alkyl" group per se and in alkoxy means a saturated or unsaturated aliphatic hydrocarbon which may be either straight- or branched-chained containing from one to about 10 carbon atoms. Lower alkyl is preferred having from one to six carbon atoms.

The "cycloalkyl" groups may be mono or polycyclic and contain 3 to 16 carbon atoms and include cyclopropyl, cyclobutyl, cyclopentyl, cyclohexyl, cycloheptyl and cyclooctyl.

"Aryl" contains from 6 to 10 carbon atoms and include phenyl, tolyl, xylyl, naphthyl and the like.

"Substituted aryl" means an aryl group substituted by one or more lower alkyl, lower alkoxy, amino, lower alkyl amino, lower alkyl mercapto, hydroxy, hydroxy lower alkyl, acetoxy, benzyloxy, phenoxy, carboxy, carboalkoxy, halo, amido, halosulfonyl, lower alkyl sulfinyl or lower alkyl sulfonyl.

"Aralkyl" means an aromatic hydrocarbon radical containing from 7 to about 16 carbon atoms and include benzyl, phenethyl, naphthylmethyl and the like.

The "heterocyclic" groups may be mono or polycyclic and include such groups as pyridyl, pyrimidinyl, quinolyl, quinolinyl, piperidyl, pyrrolyl, morpholinyl, thiomorpholinyl, thiophenyl, furyl, furfuryl, thienyl, imidazolyl, benzimidazolyl, and the like. These groups may carry substitutents such as alkyl, alkenyl, alkynyl, hydroxy, thio, amino, alkylamino, dialkylamino, alkoxy, alkylthio and halo.

"Lipophilic" means a moiety having from about 1 to about 22 carbon atoms in the entire group and includes substituted or unsubstituted, straight-or branched-chain alkyl, cycloalkyl, neopentyl, nonyl, isononyl, alkyladamantyl, 2,4-dimethylbenzyl, substituted or unsubstituted phenyl, such as 2,4-di-t-pentylphenyl or 2-naphthyl.

When $R^2$ is substituted aryl it can have up to five of the lipophilic substituents described under "lipophilic" above or any combination of members of said lipophilic group with a polar substituent, such as cyano, amino, hydrazino, acetylhydrazino, arylazo, fiuorosulfonyl or carboxamido.

"Halogen" means Cl, F, I or Br.

Preferred compounds of this invention are aryloxyphenols having the structure of Formula II:

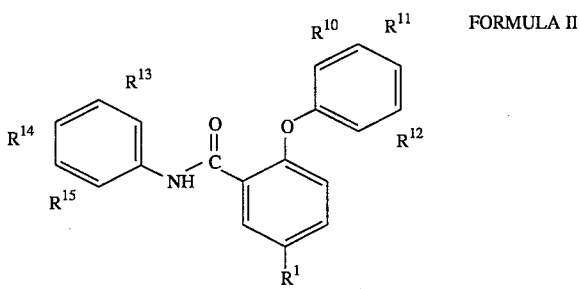

FORMULA II wherein
$R^1$ is —OH;

$R^{10}$, $R^{11}$ and $R^{12}$ are independently H or a lipophilic group, or any two of $R^{10}$, $R^{11}$ and $R^{12}$ can be taken together with the phenyl nucleus to which they are attached to form a β-naphthyl group; and $R^{13}$, $R^{14}$ and $R^{15}$ are independently H, a lipophilic group or a polar group.

Still more preferred compounds are: 2-(2,4-bis(1,1-dimethylpropyl) phenoxy)-5-hydroxybenzanilide, 3'-carboethoxy-ethyl-2-(2,4-bis( 1,1-dimethyl-propyl)phenoxy)-5-hydroxy-benzanilide, 3'-(2-hydroxyethyl)- 2-(2,4-bis(1,1-dimethylpropyl) phenoxy)-5-hydroxybenzanilide, 3'-hydroxymethyl-2-(2,4-bis(1,1-dimethylpropyl)phenoxy)- 5-hydroxybenzanilide, 3'-(1-methyl-2-carboethoxyethyl)-2-(2,4-bis( 1,1-dimethylpropyl) phenoxy)-5-hydroxy-benzanilide, 4'-iodo-2-(2,4-bis( 1,1-dimethylpropyl) phenoxy)-5-hydroxy-benzanilide, 2'-chloro-5'-(1-oxo-2-carboethoxyethyl)-2-(2,4-bis(1,1-dimethylpropyl)phenoxy)- 5-hydroxybenzanilide, 2',5'-bis(1,1-dimethylethyl)-2-(2,4-bis( 1,1-dimethylpropyl)phenoxy)-5-hydroxybenzanilide, 3',5'-dichloro-2-(2,4-bis( 1,1-dimethylpropyl) phenoxy)-5-hydroxybenzanilide, 3,'5'-dicarbomethoxy-2-(2,4-bis(1,1-dimethyl-propyl)phenoxy)-5-hydroxy-benzanilide, 3',5'-bis(1,1-dimethylethyl)-5-hydroxy-2-phenoxy-benzanilide, N-(methyl)- 2-(2,4-bis(1,1-dimethylpropyl)phenoxy)-5-hydroxy-benzamide, N-(dimethylamino)-2-(2,4-bis(1,1-dimethylpropyl)phenoxy)-5-hydroxybenzamide, N-(ethyl)-2-(2,4-bis(1,1-dimethylpropyl)phenoxy)-5-hydroxybenzamide, N-(1-methylethyl)-2-(2,4-bis(1,1-dimethylpropyl) phenoxy)-5-hydroxybenzamide, N-(1,1-dimethylethyl)-2-(2,4-bis( 1,1-dimethylpropyl)phenoxy)-5-hydroxybenzamide, S-(N-alpha-chloromethylbenzyl)-2-(2,4-bis(1,1-dimethylpropyl)phenoxy)- 5-hydroxybenzamide, N-(1-adamantyl)-2-(2,4-bis(1,1-dimethylpropyl) phenoxy)-5-hydroxybenzamide, N-(2-pyrimidinyl)-2-(2,4-bis( 1,1-dimethylpropyl)phenoxy)-5-hydroxybenzamide, N-(1,1-dimethylpropyl)- 2-(2,4-bis(1,1-dimethylpropyl)phenoxy)-5-hydroxybenzamide and N-( 1,1-dimethylpropyl)-2-(2,4-bis(1,1-dimethylpropyl)phenoxy)benzthioamide.

The compounds of the present invention may be prepared by art recognized procedures from known starting materials available from chemical supply houses (such as Aldrich Chemical Company). The following schemes illustrate such preparative procedures:

The phenolic acid 6 was successfully obtained by treatment of 4 with 31% HBr in acetic acid at reflux.

SCHEME 1

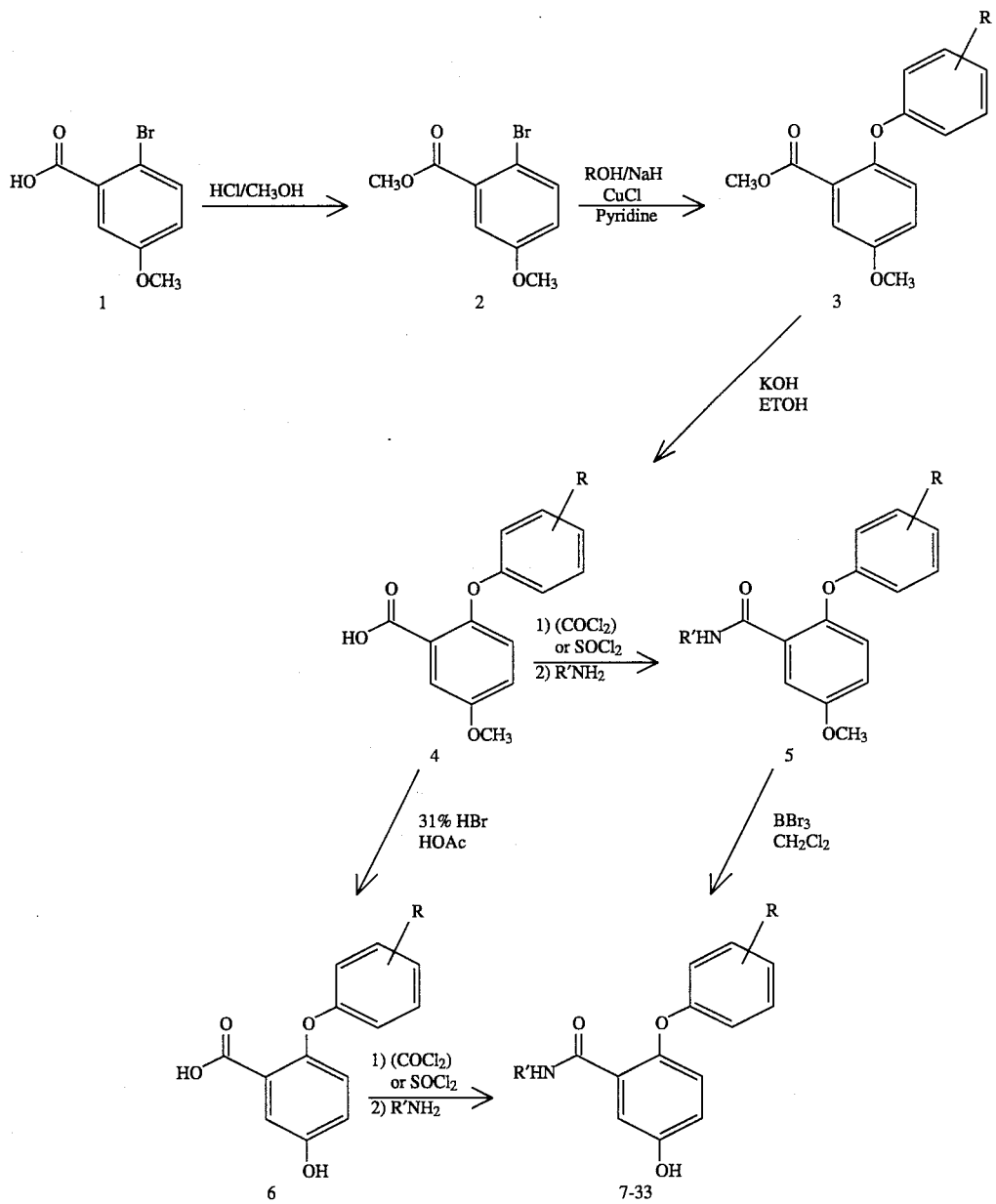

Scheme 1 describes the synthetic pathway to the desired 5-hydroxyl materials. Commercially available 2-bromo-5-methoxybenzoic acid 1 was converted to the corresponding methyl ester 2. The aryl ether 3 was prepared from 2 and the desired phenol or alcohol through a modified Ullmann coupling using cuprous chloride and pyridine. Base hydrolysis of the ester yielded acid 4 which allowed several approaches to the desired products. Formation of the acid chloride of 4 with oxalyl chloride or thionyl chloride and subsequent reaction with the desired amine afforded the amide 5. Deprotection of the methyl ether with $BBr_3$ in methylene chloride yielded the desired phenols 7–33 (Tables 1 and 2) in generally good yield.

Formation of the acid chloride of 6 was accomplished with oxalyl chloride without detriment to the hydroxyl group. Subsequent reaction with the desired amine afforded the desired phenolic amides 7–33 in good yield. Tables 1 and 2 list the materials which could be prepared using this methodology.

TABLE 1

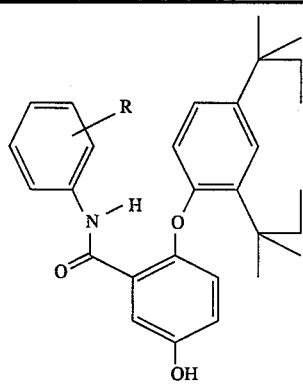

| COMPOUND NO. | R |
|---|---|
| 7 | H |
| 8 | 2-COOH |
| 9 | 3-CH(CH$_3$)CH$_2$COOH |
| 10 | 3-CH$_2$COOCH$_2$CH$_3$ |
| 11 | 3-CH$_2$CH$_2$OH |
| 12 | 3-CH$_2$COOH |
| 13 | 3-CH$_2$OH |
| 14 | 3-CH(CH$_3$)CH$_2$COOCH$_2$CH$_3$ |
| 15 | 4-I |
| 16 | 2-Cl-5-COCH$_2$COOCH$_2$CH$_3$ |
| 17 | 2,5-(C(CH$_3$)$_3$)$_2$ |
| 18 | 3,5-Cl$_2$ |
| 19 | 3,5-(COOCH$_3$)$_2$ |
| 20 | 3,5-(C(CH$_3$)$_3$)$_2$ |

TABLE 2

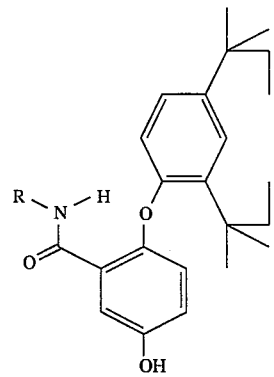

| COMPOUND NO. | R |
|---|---|
| 21 | CH$_3$ |
| 22 | N(CH$_3$)$_3$ |
| 23 | CH$_2$CH$_3$ |
| 24 | CH(CH$_3$)$_2$ |
| 25 | C(CH$_3$)$_3$ |
| 26 | C(CH$_3$)$_2$CH$_2$CH$_3$ |
| 27 | C(CH$_2$OH)$_3$ |
| 28 (a) | CH(CH$_2$OH)-phenyl |
| 29 (b) | CH(CH$_2$OH)-phenyl |
| 30 (a) | CH(CH$_2$Cl)-phenyl |
| 31 (b) | CH(CH$_2$Cl)-phenyl |
| 32 | 1-Adamantyl |
| 33 | 2-Pyrimidinyl |

(a) R isomer
(b) S isomer

Compound 34, 35, 36 and 37 shown in Table 3 can be made using the following scheme:

SCHEME 2

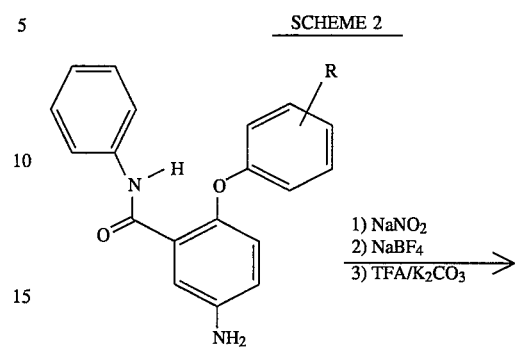

TABLE 3

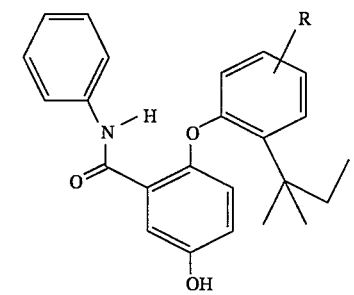

| COMPOUND NO. | R |
|---|---|
| 34 | C(CH$_3$)$_2$CH$_2$CH$_3$ |
| 35 | H |
| 36 | C(CH$_3$)$_3$ |
| 37 | 2,4,6-(CH$_3$)$_3$ |

The following preparative examples will further illustrate the invention.

PREPARATION OF INTERMEDIATE

Methyl 2-(2,4-di-tert-pentylphenoxy)-5-methoxymethyl-benzoate

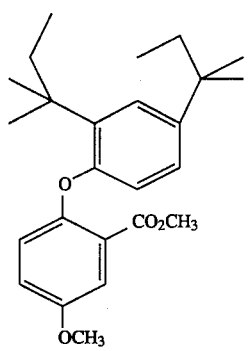

To a solution of sodium hydride (1.2 g, 0.05 mol) in pyridine (60 mL), was added a solution of 2,4-di-tert-pentlyphenol (12.9 g, 0.055 mol) in pyridine (20 mL) with stirring. Gas evolution ceased in approximately 1.5 hr at which time methyl 2-bromo-5-methoxylbenzoate was added. Copper (I) chloride (1.24 g, 0.0126 mol) was added and the mixture heated to reflux for 8 hours. The reaction mixture was diluted with diethyl ether (100 mL) and washed with 3N HCl (3×50 mL) and then washed with saturated sodium bicarbonate (1×50 mL). The organic extracts were dried over sodium sulfate, filtered and concentrated to give a dark oil. Chromatography on silica gel with 1:1 heptane:ethyl acetate yielded the pure product as a viscous oil in 90% yield. NMR and mass spectral analysis were consistent with proposed structure.

2-(2,4-di-tert-pentylphenoxy)-5-methoxybenzoic acid

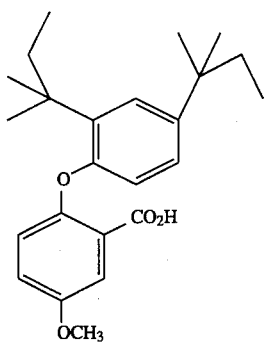

To a solution of potassium hydroxide (5.6 g, 0.1 mol) in ethanol (150 mL) was added methyl 2-(2,4-di-tert-pentylphenoxy)-5-methoxybenzoate (18.0 g, 0.045 mol) and the mixture brought to reflux for 2 hours. TLC indicated the hydrolysis to be complete. The ethanol was removed in vacuo and the residue taken up in water (75 mL) and acidified with 6N HCl. The aqueous mixture was extracted with ethyl acetate (3×100 mL). The organic layers were combined and dried over magnesium sulfate, filtered and the solvent removed in vacuo. Recrystallization from heptane yielded the product as a white solid in 90% yield. NMR and mass spectral analysis were consistent with proposed structure.

2-(2,4-di-tert-pentylphenoxy)-5-hydroxybenzoic acid

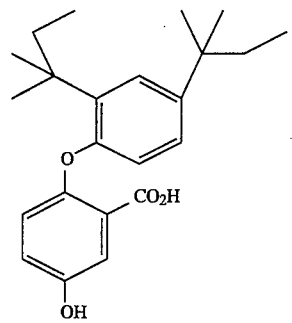

A solution of 2-(2,4-di-tert-pentylphenoxy)-5-methoxybenzoic acid (10.0 g, 0.026 mol) in 31% HBr/HOAc (100 mL) was heated to reflux for 1 hour. The reaction mixture was cooled to room temperature and added to 500 mL water. The mixture was extracted with ethyl acetate (3×200 mL), and the combined organic extracts repeatedly washed with water to remove traces of acid. The organic extracts were dried over magnesium sulfate and concentrated to give a tan solid. Chromatography on silica gel with 1:1 heptane:ethyl acetate yielded the product in 80% yield. NMR and mass spectral data were consistent with the proposed structure.

EXAMPLE 1

2-(2,4-di-tert-pentylphenoxy)-5-hydroxybenzanilide

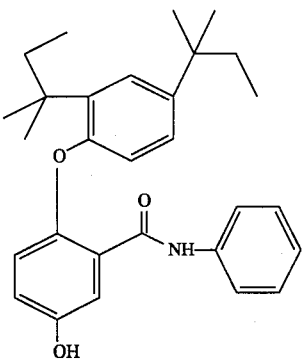

A solution of 2-(2,4-di-tert-pentylphenoxy)-5-hydroxybenzoic acid (3.3 g, 8.9 mmol) and oxalyl chloride (1.25 g, 9.8 mmol) in dichloromethane (75 mL) was stirred at room temperature for 2 hours. The solvent was removed in vacuo and the residue triturated with toluene (25 mL) followed by distillation of the solvent. The crystalline residue was taken up in dichloromethane (80 mL) and aniline (1.66 g, 17.9 mmol) was added. The reaction mixture was allowed to stir at room temperature for 8 hours, then submitted to aqueous, acidic workup. Flash column chromatography on silica gel with 90:10 heptane:ethyl acetate yielded the addition product. Recrystallization from heptane/ethyl acetate yielded analytically pure product in 79% overall yield.

EXAMPLE 2

N-tert-butyl-2-(2,4-di-tert-pentylphenoxy)-5-hydroxybenzamide

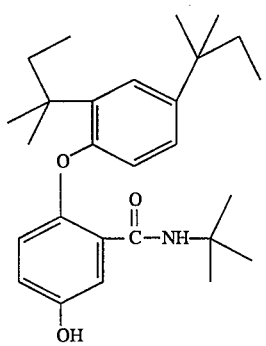

A solution of 2-(2,4-di-tert-pentylphenoxy)-5-methoxybenzoic acid (1.0 g, 2.6 mmol) and oxalyl chloride (0.34 g, 3 mmol) in dichloromethane (25 mL) was stirred at room temperature for 2 hours. The solvent was removed in vacuo and the residue triturated with toluene (25 mL) followed by distillation of the solvent. The crystalline residue was taken up in dichloromethane (50 mL) and tert-butylamine (0.22 g, 3.0 mmol) and triethylamine (0.4 g, 4 mmol) were added. The reaction mixture was allowed to stir at room temperature for 8 hours, then submitted to aqueous, acidic workup. Flash column chromatography on silica gel with heptane yielded the pure addition product. Demethylation of the 5-methoxy group to give the hydroxy derivative was achieved by dissolving the solid in dichloromethane (50 mL) and adding boron tribromide (1 M in dichloromethane, 2.5 equivalents) at 0° C. with stirring for 1.5 hours. The mixture was submitted to aqueous workup and extracted with diethyl ether (3×50 mL). Removal of the solvent in vacuo yielded the desired product in 86% overall yield.

EXAMPLE 3

N-tert-pentyl-2-(2,4-di-tert-pentylphenoxy)-5-hydroxybenzamide

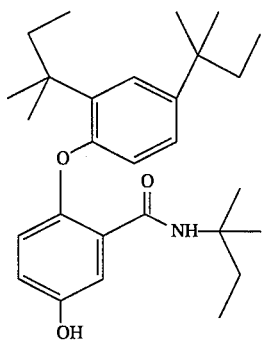

A solution of 2-(2,4-di-tert-pentylphenoxy)-5-methoxybenzoic acid (1.0 g, 2.6 mmol), and oxalyl chloride (0.34 g, 3 mmol) in dichloromethane (25 mL) was stirred at room temperature for 2 hours. The solvent was removed in vacuo and the residue triturated with toluene (25 mL) followed by distillation of the solvent. The crystalline residue was taken up in dichloromethane (50 mL) and tert-pentylamine (0.26 g, 3.0 mmol) and triethylamine (0.4 g, 4 mmol) added. The reaction mixture was allowed to stir at room temperature for 8 hours, then submitted to aqueous, acidic workup. Flash column chromatography on silica gel with heptane yielded the pure addition product. Demethylation of the 5-methoxy group to give the hydroxy derivative was achieved by dissolving the solid in dichloromethane (50 mL) and adding boron tribromide (1 M in dichloromethane, 2.5 equivalents) at 0° C., with stirring, for 1.5 hours. The mixture was submitted to aqueous workup and extracted with diethyl ether (3×50 mL). Removal of the solvent in vacuo yielded the desired product in 85% overall yield.

EXAMPLE 4

N-(1-adamantyl)-2-(2,4-di-tert-pentylphenoxy)-5-hydroxybenzamide

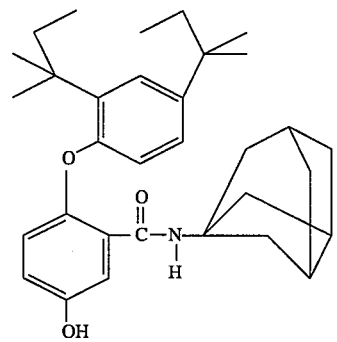

A solution of 2-(2,4-di-tert-pentylphenoxy)-5-methoxybenzoic acid (1.0 g, 2.6 mmol) and oxalyl chloride (0.34 g, 3 mmol) in dichloromethane (25 mL) was stirred at room temperature for 2 hours. The solvent was removed in vacuo and the residue triturated with toluene (25 mL) followed by distillation of the solvent. The crystalline residue was taken up in dichloromethane (50 mL) and 1-adamantylamine hydrochloride (0.48 g, 2.6 mmol) and triethylamine (0.56 g, 5.4 mmol) added. The reaction mixture was allowed to stir at room temperature for 2 hours, then submitted to aqueous, acidic workup. Flash column chromatography on silica gel with 4:1 heptane:ethyl acetate yielded the pure addition product. Demethylation of the 5-methoxy group to give the hydroxy derivative was achieved by dissolving the solid in dichloromethane (50 mL) and adding boron tribromide (1 M in dichloromethane, 2.5 equivalents) at 10° C., with stirring, for 3 hours. The mixture was submitted to aqueous workup and extracted with diethyl ether (3×50 mL). Removal of the solvent in vacuo yielded the desired product in 81% overall yield.

EXAMPLE 5

1-(3',5'-dicarbomethoxy)-2-(2,4-di-tert-pentylphenoxy)-5-hydroxy benzanilide

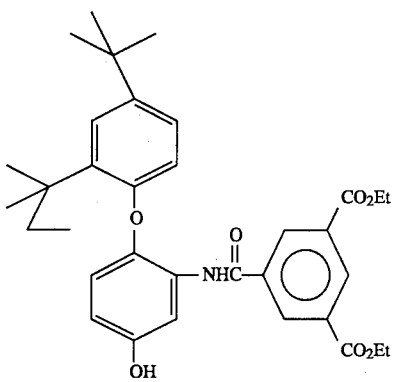

A solution of 2-(2,4-di-tert-pentylphenoxy)-5-methoxybenzoic acid (1.0 g, 2.6 mmol) and oxalyl chloride (0.36 g, 3 mmol) in dichloromethane (25 mL) was stirred at room temperature for 2 hours. The solvent was removed in vacuo and the residue triturated with toluene (25 mL) followed by distillation of the solvent. The crystalline residue was taken up in dichloromethane (50 mL) and dimethyl 5-aminoisophthalate (0.54 g, 2.6 mmol) and triethylamine (0.4 g, 4 mmol) added. The reaction mixture was allowed to stir at room temperature for 8 hours, then submitted to aqueous, acidic workup. Flash column chromatography on silica gel with 1:3 ethyl acetate:heptane yielded the pure addition product. Demethylation of the 5-methoxy group to give the hydroxy derivative was achieved by dissolving the solid in dichloromethane (50 mL) and adding boron tribromide (1 M in dichloromethane, 2.5 equivalents) at room temperature with stirring for 2 hours. The mixture was submitted to aqueous workup and extracted with diethyl ether (3×50 mL). Removal of the solvent in vacuo yielded the desired product in 76% overall yield.

The biological profile of the compounds of the present invention include the following characteristics:

(a) Induction of secretion of IL-2 by murine EL-4 cells at concentrations as low as $4 \times 10^{-8}$ M;

(b) Induction of IL-2 and granulocytes macrophage colony stimulating factor (GM-CSF) gene expression in EL-4 cells;

(c) Production of IL-3 and IL-4;

(d) Lack of binding IL-1, IL-2 or IL-4 receptors; neither agonists or antagonists to these lymphokines;

(e) Induction of proliferation of human thymocytes;

(f) Induction of proliferation of human T-cells and B-cells and murine T-cells;

(g) No indication of toxicity when administered IP, PO or IV; and (h) Enhancement of human mixed lymphocyte reaction in a dose-dependent manner.

Based on these findings, the compounds of the present invention are useful for prophylaxis and therapy of immunological diseases. According to the kind of diseases, to the condition of the patients and to the immune state, the physician will determine the amount of the drug to be administered, the frequency of administration, routes of administration and vehicles containing the compounds to be administered.

The compounds of this invention can be normally administered parenterally, in the prophylaxis and treatment of immunological disorders.

The compounds of this invention, or salts thereof, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents.

For parenteral administration, solutions or suspensions of these compounds in aqueous alcoholic media or in sesame or peanut oil or aqueous solutions of the soluble pharmaceutically acceptable salts described herein can be employed. Solutions of the salts of these compounds are especially suited for intramuscular and subcutaneous injection purposes. The aqueous compositions, including solutions of the salts dissolved in pure distilled water are also useful for intravenous injection purposes, provided that their pH is properly adjusted, suitably buffered, made isotonic with sufficient saline or glucose and sterilized by heating or by microfiltration. Certain compositions useful for intravenous injection or infusion may be prepared using the solid form of the active compound of the present invention. The solid compound may be suspended in propylene glycol, or a polyethylene glycol ether such as PEG 200, using a sonicator and the resulting mixture combined with aqueous media.

The dosage regimen in carrying out the methods of this invention is that which insures maximum therapeutic response until improvement is obtained and thereafter the minimum effective level which gives relief. It should be borne in mind that selecting the appropriate dosage in any specific case, consideration must be given to the patient's weight, general health, age and other factors which may influence response to the drug. The drug may be administered as frequently as is necessary to achieve and sustain the desired therapeutic response.

The present invention is also useful as an injectable dosage form which may be administered in an emergency to a patient. Such treatment may be followed by intravenous infusion of the active compound and the amount of compound infused into such patient should be effective to achieve and maintain the desired therapeutic response.

About 10 to 500 mg of a compound or mixture of compounds of formula (I) or pharmaceutically acceptable salts thereof is compounded with a physiologically acceptable vehicle, carrier, excipient, binder, preservative, stabilizer and flavor in a unit dosage form as called for by accepted pharmaceutical practice. The amount of active substance in these compositions or preparations is such that a suitable dosage in the following range indicated is obtained. A single dose, or preferably two to four divided daily doses, provided on a basis of about 0.1 to 100 mg per kilogram of body weight per day, preferably about 1 to 50 mg per kilogram of body weight per day is appropriate to introduce to a mammal for immunostimulation.

The following test results illustrate the beneficial effects of compounds of the present invention.

IL-1 BIOASSAY

EL-4 6.1 cells (murine T-cells) were first treated with mitomycin C to inhibit their proliferation. After washing the cells free of mitomycin C, the test compound ($10^{-5}$ M) or the IL-1 standard ($3 \times 10^{-11}$ M) was incubated with $2 \times 10^5$ EL-4 6.1 cells for 24 hours to allow gene expression and IL-2 synthesis. To quantify IL-2 production, CTLL-2 cells (IL-2 hybridized mouse cytotoxic T cell line which requires IL-2 for growth) were added and incubated for 24 hours; then tritiated thymidine was added and the cells incubated an additional 4 hours. The cells were then collected by centrifugation through oil and counted. Screening results were reported relative to the IL-1 standard run concurrently. Activity was considered to be >20% cell proliferation of the IL-1 standard as determined by thymidine uptake. Positive compounds that demonstrated reproducible biological activity were then tested for a dose response at $10^{-5}$, $3\times10^{-6}$, $10^{-6}$, $4\times10^{-7}$ M and $4\times10^{-8}$ M. The result in Table 4 gives the activity indicated where the numbers refer to compound numbers and the activity key is as shown:

TABLE 4

| COMPOUND NO. | ACTIVITY |
| --- | --- |
| 7 | ++++ |
| 10 | ++++ |
| 11 | +++ |
| 12 | + |
| 13 | ++++ |
| 14 | ++++ |
| 15 | ++++ |
| 16 | ++++ |
| 17 | +++ |
| 18 | ++++ |
| 19 | +++++ |
| 20 | +++ |
| 21 | ++++ |
| 22 | +++ |
| 23 | ++++ |
| 24 | ++++ |
| 25 | +++++ |
| 26 | +++++ |
| 27 | ++ |
| 28 | ++ |
| 29 | + |
| 30 | ++ |
| 31 | +++ |
| 32 | +++++ |
| 33 | +++ |
| 35 | ++ |
| 36 | ++ |
| 37 | + |

+ Active at $10^{-5}$ M
++ Active at $3 \times 10^{-6}$ M
+++ Active at $10^{-6}$ M
++++ Active at $4 \times 10^{-7}$ M
+++++ Active at $10^{-7}$ M
++++++ Active at $4 \times 10^{-8}$ M It should be understood by those skilled in the art that various modifications may be made in the present invention without departing from the spirit and scope thereof as described in the specification and defined in the appended claims.

What is claimed is:

1. A method for inducing the production of interleukin-2 in a warm-blooded animal in need of such interleukin-2 production to combat bacterial or viral infections which comprises parenterally administering an effective amount of a compound of formula (I) or a pharmaceutically acceptable salt thereof:

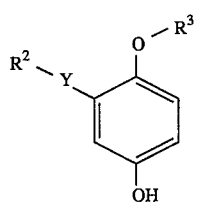

FORMULA I wherein
Y is

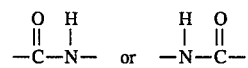

$R^2$ is H or substituted or unsubstituted $C_6$–$C_{10}$ aryl, wherein said substituents are selected from the group consisting of lower alkyl, lower alkoxy, amino, lower alkyl amino, lower alkyl mercapto, hydroxy or hydroxy lower alkyl; and $R^3$ is a lipophilic moiety selected from the group consisting of substituted $C_1$–$C_{10}$ alkyl, $C_3$–$C_{16}$ cycloalkyl and 2,4-di-t-pentylphenyl.

2. The method of claim 1 wherein said compound is selected from the group consisting of 2-(2,4-bis(1,1-dimethylpropyl)phenoxy)-5-hydroxybenzanilide, 3'-carboethoxyethyl-2-(2,4-bis(1,1-dimethyl-propyl)phenoxy)-5-hydroxybenzanilide, 3'-(2-hydroxyethyl)-2-(2,4-bis(1,1-dimethylpropyl)-phenoxy)-5-hydroxybenzanilide, 3'-hydroxymethyl-2-(2,4-bis(1,1-dimethylpropyl)phenoxy)-5-hydroxybenzanilide, and 3'-(1-methyl-2-carboethoxyethyl)-2-(2,4-bis(1,1-dimethylpropyl)phenoxy)- 5-hydroxybenzanilide.

3. The method of claim 1 wherein said compound is selected from the group consisting of 4'-iodo-2-(2,4-bis(1,1-dimethylpropyl)phenoxy)-5-hydroxy-benzanilide, 2'-chloro-5'-(1-oxo-2-carboethoxyethyl)-2-(2,4-bis(1,1-dimethylpropyl)phenoxy)- 5-hydroxybenzanilide, 2',5'-bis(1,1-dimethylethyl)-2-(2,4-bis( 1,1-dimethylpropyl)phenoxy)-5-hydroxybenzanilide, 3',5'-dichloro-2-(2,4-bis( 1,1-dimethyl-propyl)phenoxy)-5-hydroxybenzanilide, and 3',5'-dicarbomethoxy-2-( 2,4-bis(1,1-dimethylpropyl)phenoxy)-5-hydroxybenzanilide.

4. The method of claim 1 wherein said compound is selected from the group consisting of 3',5'-bis(1,1-dimethylethyl)-5-hydroxy-2-phenoxybenzanilide, N-(methyl)-2-(2,4-bis(1,1-dimethylpropyl)-phenoxy)-5-hydroxybenzamide, N-(dimethylamino)-2-(2,4-bis(1,1-dimethylpropyl)phenoxy)-5-hydroxy-benzamide, N-(ethyl)-2-(2,4-bis(1,1-dimethylpropyl)phenoxy)-5-hydroxybenzamide and N-( 1-methylethyl)-2-(2,4-bis(1,1-dimethylpropyl)phenoxy)-5-hydroxybenzamide.

5. The method of claim 1 wherein said compound is selected from the group consisting of N-(1,1-dimethylethyl)-2-(2,4-bis(1,1-dimethylpropyl)-phenoxy)- 5-hydroxybenzamide, N-(1,1-dimethyl-propyl)-2-(2,4-bis( 1,1-dimethylpropyl)phenoxy)-5-hydroxy-benzamide, N-((1,1,1-trihydroxymethyl) methyl)-2-( 2,4-bis(1,1-dimethylpropyl)phenoxy)-5-hydroxybenzamide, R-(N-alpha-hydroxymethylbenzyl)-2-(2,4-bis(1,1-dimethylpropyl)phenoxy)- 5-hydroxybenzamide and R-(N-alpha-chloromethylbenzyl)-2-(2,4-bis( 1,1-dimethylpropyl)phenoxy)-5-hydroxybenzamide.

6. The method of claim 1 wherein said compound is selected from the group consisting of S-(N-alpha-chloromethylbenzyl)-2-(2,4-bis(1,1-dimethylpropyl) phenoxy)-5-hydroxybenzamide, N-(1-adamantyl)-2-(2,4-bis( 1,1-dimethyl-propyl)phenoxy)-5-hydroxybenzamide, N-(2-pyrimidinyl)-2-(2,4-bis ( 1,1-dimethylpropyl)phenoxy)-5-hydroxybenzamide, 5-hydroxy-2-(phenoxy)-benzanilide and 5-hydroxy-2-(2-(1,1-dimethylethyl)phenoxy)-benzanilide.

7. A method for inducing the production of interleukin-2 in a warm-blooded animal in need of such interleukin-2 production to combat bacterial or viral infections which comprises parenterally administering an effective amount of a pharmaceutical composition comprising a compound of the formula (I) in combination with a pharmaceutically acceptable carrier:

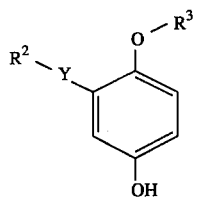

FORMULA I wherein
Y is

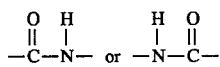

$R^2$ is H or substituted or unsubstituted $C_6$–$C_{10}$ aryl, wherein said substituents are selected from the group consisting of lower alkyl, lower alkoxy, amino, lower alkyl amino, lower alkyl mercapto, hydroxy or hydroxy lower alkyl; and $R^3$ is a lipophilic moiety selected from the group consisting of substituted $C_1$–$C_{10}$ alkyl, $C_3$–$C_{16}$ cycloalkyl and 2,4-di-t-pentylphenyl.

8. The method of claim 7 wherein said compound is selected from the group consisting of 2-(2,4-bis(1,1-dimethylpropyl)phenoxy)- 5-hydroxybenzanilide, 3'-carboethoxyethyl-2-(2,4-bis(1,1-dimethyl-propyl)phenoxy)- 5-hydroxybenzanilide, 3'-(2-hydroxyethyl)-2-(2,4-bis(1,1-dimethylpropyl)-phenoxy)- 5-hydroxybenzanilide, 3'-hydroxymethyl-2-(2,4-bis(1,1-dimethylpropyl)phenoxy)-5-hydroxybenzanilide, and 3'-(1-methyl-2-carboethoxyethyl)-2-(2,4-bis( 1,1-dimethylpropyl)phenoxy)-5-hydroxybenzanilide.

9. The method of claim 7 wherein said compound is selected from the group consisting of 4'-iodo-2-(2,4-bis( 1,1-dimethylpropyl)phenoxy)-5-hydroxy-benzanilide, 2'-chloro-5'-(1-oxo- 2-carboethoxyethyl)-2-(2,4-bis(1,1-dimethylpropyl)phenoxy)-5-hydroxybenzanilide, 2',5'-bis(1,1-dimethylethyl)-2-(2,4-bis(1,1-dimethylpropyl)phenoxy)- 5-hydroxybenzanilide, 3',5'-dichloro-2-(2,4-bis(1,1-dimethyl-propyl)phenoxy)- 5-hydroxybenzanilide, and 3',5'-dicarbomethoxy-2-(2,4-bis( 1,1-dimethylpropyl)phenoxy)-5-hydroxybenzanilide.

10. The method of claim 7 wherein said compound is selected from the group consisting of 3',5'-bis(1,1-dimethylethyl)-5-hydroxy- 2-phenoxybenzanilide, N-(methyl)-2-(2,4-bis(1,1-dimethylpropyl)-phenoxy)- 5-hydroxybenzamide, N-(dimethylamino)-2-(2,4-bis(1,1-dimethylpropyl)phenoxy)- 5-hydroxy-benzamide, N-(ethyl)-2-(2,4-bis(1,1-dimethylpropyl)phenoxy)-5-hydroxybenzamide and N-(1-methylethyl)-2-(2,4-bis(1,1-dimethylpropyl)phenoxy)- 5-hydroxybenzamide.

11. The method of claim 7 wherein said compound is selected from the group consisting of N-(1,1-dimethylethyl)-2-(2,4-bis( 1,1-dimethylpropyl)-phenoxy)-5-hydroxybenzamide, N-(1,1-dimethyl-propyl)-2-( 2,4-bis(1,1-dimethylpropyl)phenoxy)-5-hydroxy-benzamide, N-((1,1,1-trihydroxymethyl) methyl)-2-(2,4-bis(1,1-dimethylpropyl)phenoxy)- 5-hydroxybenzamide, R-(N-alpha-hydroxymethylbenzyl)-2-(2,4-bis( 1,1-dimethylpropyl)phenoxy)-5-hydroxybenzamide and R-(N-alpha-chloromethylbenzyl)-2-(2,4-bis(1,1-dimethylpropyl)phenoxy)- 5-hydroxybenzamide.

12. The method of claim 7 wherein said compound is selected from the group consisting of S-(N-alpha-chloromethylbenzyl)-2-( 2,4-bis(1,1-dimethyl-propyl)phenoxy)-5-hydroxybenzamide, N-(1-adamantyl)-2-( 2,4-bis(1,1-dimethyl-ethyl-propyl)phenoxy)-5-hydroxybenzamide, N-(2-pyrimidinyl)-2-( 2,4-bis (1,1-dimethylpropyl)phenoxy)-5-hydroxybenzamide, 5-hydroxy-2-(phenoxy)-benzanilide and 5-hydroxy-2-(2-(1,1-dimethylethyl)phenoxy)-benzanilide.

* * * * *